(12) United States Patent
Sliski et al.

(10) Patent No.: US 6,421,416 B1
(45) Date of Patent: Jul. 16, 2002

(54) APPARATUS FOR LOCAL RADIATION THERAPY

(75) Inventors: Alan P. Sliski, Lincoln; Kenneth J. Harte, Carlisle, both of MA (US)

(73) Assignee: Photoelectron Corporation, Lexington, MA (US)

(*) Notice: Subject to any disclaimer, the term of this patent is extended or adjusted under 35 U.S.C. 154(b) by 0 days.

(21) Appl. No.: 09/502,759

(22) Filed: Feb. 11, 2000

(51) Int. Cl.[7] .................................................. A61N 5/10
(52) U.S. Cl. .............................. 378/65; 378/64; 378/145
(58) Field of Search ........................... 378/65, 64, 145; 607/51; 604/1, 20

(56) References Cited

U.S. PATENT DOCUMENTS

| | | |
|---|---|---|
| 3,752,990 A | 8/1973 | Fischer |
| 4,646,338 A | 2/1987 | Skillicorn |
| 4,694,480 A | 9/1987 | Skillicorn |
| 5,090,043 A * | 2/1992 | Parker et al. ............... 378/121 |
| 5,153,900 A | 10/1992 | Nomikos et al. |
| 5,165,093 A | 11/1992 | Miller et al. |
| RE34,421 E | 10/1993 | Parker et al. |
| 5,369,679 A | 11/1994 | Sliski et al. |
| 5,422,926 A | 6/1995 | Smith et al. |
| 5,442,678 A | 8/1995 | Dinsmore et al. |
| 5,528,652 A | 6/1996 | Smith et al. |
| 5,566,221 A * | 10/1996 | Smith et al. ................ 378/145 |
| 5,621,780 A | 4/1997 | Smith et al. |
| 5,748,699 A * | 5/1998 | Smith |

* cited by examiner

Primary Examiner—Drew Dunn
Assistant Examiner—Pamela R. Hobden
(74) Attorney, Agent, or Firm—McDermott, Will & Emery

(57) ABSTRACT

A radiation applicator system is structured to be mounted to a radiation source for producing a predefined dose of radiation for treating a localized volume of tissue, such as the tissue surrounding the site of an excised tumor. The applicator system includes an applicator and, in some embodiments, an adapter. The adapter is formed for fixedly securing the applicator to a radiation source, such as the x-ray source of a radiosurgery system which produces a predefined radiation dose profile with respect to a predefined location along its radiation producing probe. The applicator includes a shank and an applicator head, wherein the head is located at a distal end of the applicator shank. A proximate end of the applicator shank couples to the adapter. A distal end of the shank includes the applicator head, which defines a concave treatment surface for engaging and, preferably, supporting the area to be treated with a predefined does of radiation. The applicator can include a low energy radiation filter inside of the applicator head to reduce undesirable low energy radiation emissions. A plurality of applicators having applicator heads of different sizes and shapes can be provided to accommodate treatment sites of various sizes and shapes. And, an adaptable applicator having a plurality of radiation positions can be provided to deliver a substantially cylindrical dose of radiation.

22 Claims, 8 Drawing Sheets

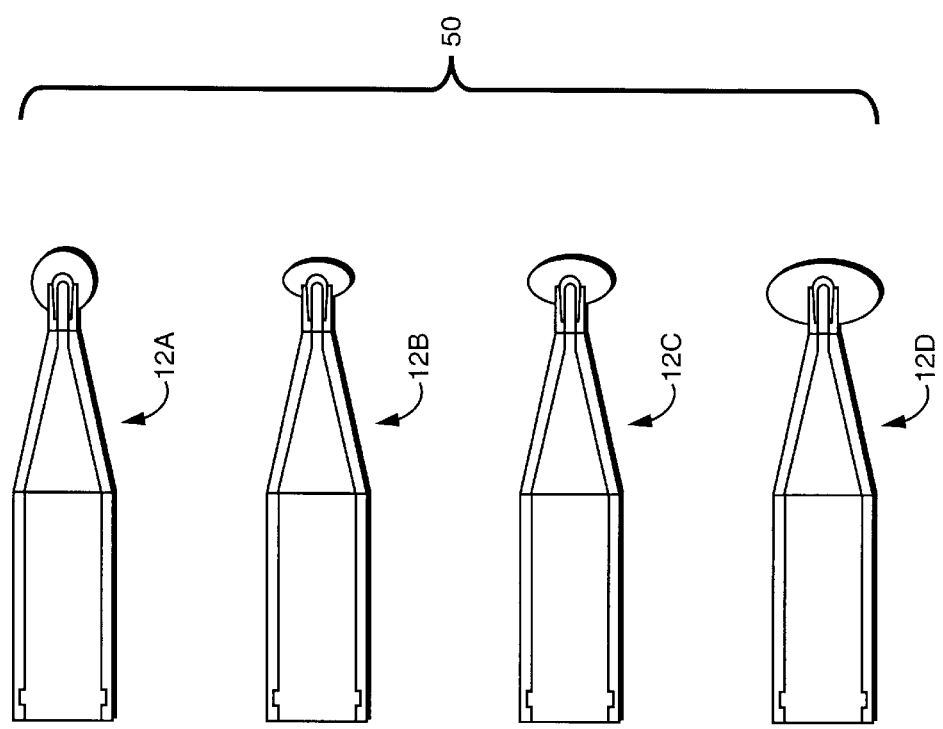

APPARATUS FOR LOCAL RADIATION THERAPY

CROSS-REFERENCE TO RELATED APPLICATIONS

Not Applicable

STATEMENT REGARDING FEDERALLY SPONSORED RESEARCH

Not Applicable

REFERENCE TO MICROFICHE APPENDIX

Not Applicable

BACKGROUND OF THE INVENTION

This invention relates to a miniaturized, programmable radiation source for use in delivering substantially constant or intermittent levels of x-rays to a specified region and, more particularly, to an apparatus for delivering a controlled dose of radiation to a localized volume of tissue, such as a volume of tissue of the human body.

In the field of medicine, radiation is used for diagnostic, therapeutic and palliative treatment of patients. The conventional medical radiation sources used for these treatments include large fixed position machines such as linear accelerators ("LINACs"), smaller transportable radiation delivery machines such as high-dose-rate after loaders, and catheters for low-dose-rate brachytherapy. The current state of the art treatment systems utilize computers to generate complex treatment plans for treating complex geometric volumes.

Typically, these systems apply doses of radiation in order to inhibit the growth of new tissue because it is known that radiation affects dividing cells more than the mature cells found in non-growing tissue. Thus, the regrowth of cancerous tissue in the site of an excised tumor can be treated with radiation to prevent the recurrence of cancer. Alternatively, radiation can be applied to other areas of the body to inhibit tissue growth, for example the growth of new blood vessels inside the eye that can cause macular degeneration.

Conventional radiation treatment systems, such as the LINAC used for medical treatment, utilize a high power remote radiation source and direct a beam of radiation at a target volume, such as a tumor inside the body of a patient. This type of treatment is referred to as teletherapy because the radiation source is located a predefined distance, typically on the order of one meter, from the target. This treatment suffers from the disadvantage that tissue disposed between the radiation source and the target is exposed to radiation.

An alternative treatment system utilizing a point source of radiation is disclosed in U.S. Pat. No. 5,153,900 issued to Nomikos et al., owned by the assignee of the present application, which is hereby incorporated by reference. The system includes a miniaturized, insertable probe capable of producing low power radiation in predefined dose geometries or profiles disposed about a predetermined location. One advantage of this system is that the radiation is applied to treat a predefined tissue volume, without significantly affecting the tissue in adjacent volumes.

A typical use of the described radiation therapy system involves positioning the insertable probe into the tumor or the site where the tumor or a portion of the tumor was removed to treat the tissue adjacent the site with radiation. In order to facilitate controlled treatment of the site, it is desirable to support the tissue portions to be treated at a predefined distance from the radiation source. Alternatively, where the treatment involves the treatment of surface tissue or the surface of an organ, it is desirable to control the shape of the surface as well as the shape of the radiation field applied to the surface.

The treatment can involve the application of radiation, either continuously or intermittently, over an extended period of time. Therefore, it is desirable that the insertable probe be adjustably supported in a compliant manner to accurately position the radiation source with respect to the treated site and accommodate normal minor movements of the patient, such as movements associated with breathing.

Accordingly, it is an object of the present invention to provide an improved system for delivering radiation to a localized region.

SUMMARY OF THE INVENTION

The present invention is directed to a radiation applicator system which is mountable to a radiation source in order to apply a predefined dose of radiation to a surface of a body to treat a volume of tissue. The radiation applicator system includes an applicator and, preferably, an adapter. When included, the adapter couples the applicator to a radiation source. The applicator includes an applicator shank and an applicator head. The adapter may take any of a variety of forms, and may, for example, be integral with the shank, the radiation source, or may include one or more separate components which couple the shank to the radiation source. The adapter may also be formed from some combination thereof. In the preferred form, the adapter is a separate component that engages the applicator shank at the shank's proximate end and thereby allows coupling of the applicator to the radiation source, when the adapter is coupled to the radiation source. At the opposite and distal end of the applicator shank is the applicator head, having a convex treatment surface adapted for applying a predefined dose of radiation across a surface contour to treat a predefined volume of tissue surrounding a surgical site. Preferably, the applicator head and surface contour coincide such that the convex surface of the applicator head engages and supports the concave surface of the volume to be treated and applies a predetermined dose of radiation across the surface to that volume.

In one embodiment, the radiation source includes an elongated probe and is adapted for producing a predefined radiation dose profile about a predetermined location with respect to the probe. In this embodiment, the applicator system can also include a low energy radiation filter adapted to surround at least a portion of the probe within the applicator head. The low energy radiation filter serves to reduce the low energy radiation produced by the probe which can damage tissue adjacent to the applicator head. The applicator head engages the area to be treated, such as the area adjacent to the site where a tumor was removed in order to permit the application of radiation to prevent the regrowth of the tumor.

Preferably, the applicator system is adapted to be mounted to the radiation source and encase the source's elongated probe to form a self-contained treatment assembly or kit. During a surgical procedure, the treatment assembly, including the applicator system and the radiation source, can be supported by a carrier system. The carrier support system can be adapted to support the treatment assembly in a substantially weightless configuration in order to facilitate positioning by the physician during surgery and to accommodate substantially minor movements by the patient, such as those caused by breathing.

BRIEF DESCRIPTION OF THE DRAWINGS

The foregoing and other objects of this invention, the various features thereof, as well as the invention itself may be more fully understood from the following descript ion, when read together with the accompanying drawings in which:

FIG. 4 is a diagrammatic cross sectional view of a plurality of applicators, as part of a kit, in accordance with another aspect of the invention;

DETAILED DESCRIPTION OF THE PREFERRED EMBODIMENTS

Figure 1A:
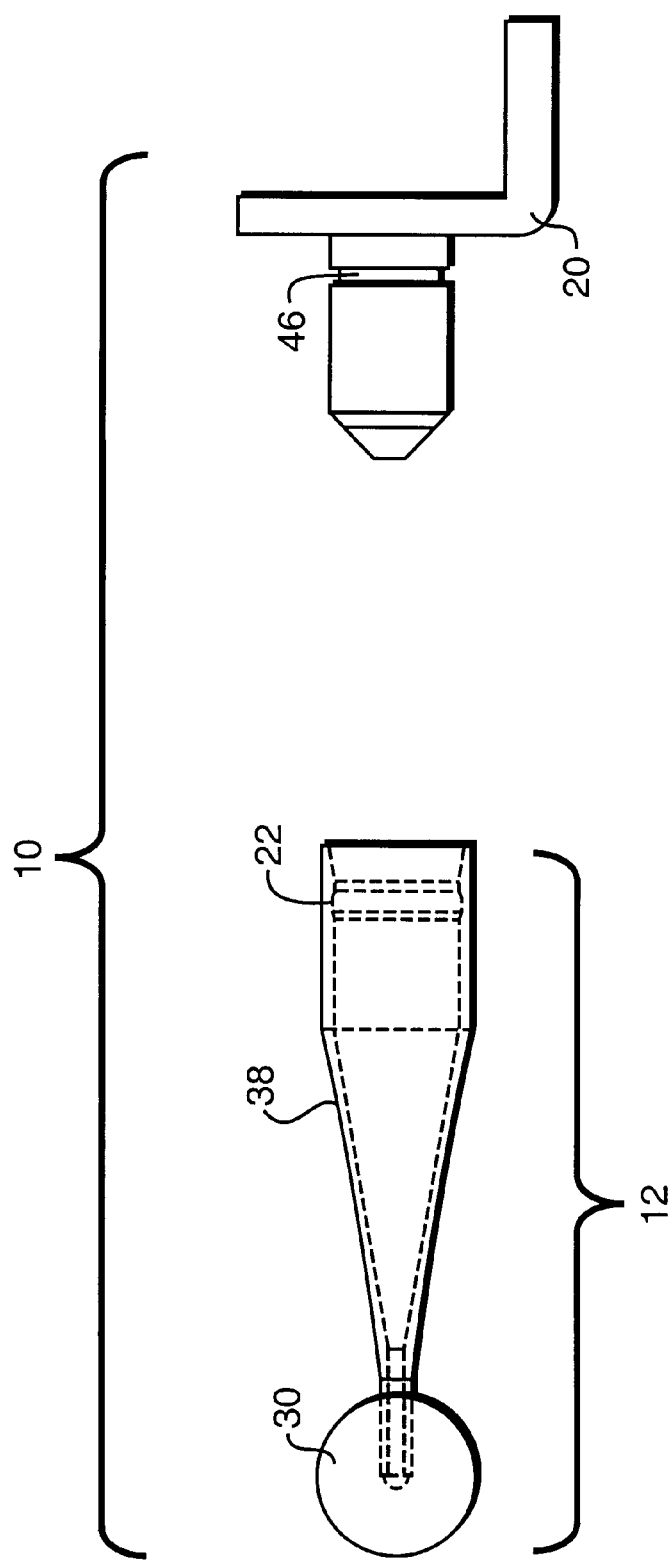
FIG. 1A is a diagrammatic exploded view of an applicator system, in accordance with the present invention.

FIG. 1A shows an applicator system 10 for applying a dose of radiation across a predefined contour of a body to treat a predefined volume of tissue. The applicator system 10 preferably includes an applicator 12 and an adapter 20, but in some embodiments an adapter may not be included. Applicator 12 includes a shank 38 and a head 30, wherein head 30 is located at a distal end of shank 38. In the preferred form, the adapter is a separate component, but in other embodiments the adapter may be integral with the shank or with the radiation source, or some combination thereof. A proximate end of shank 38 removably engages with adapter 20 to form the preferred applicator system 10. Adapter 20 is structured for attaching applicator system 10 to a radiation source (not shown). At the opposite end of shank 38, applicator head 30 includes a convex surface adapted for engaging and conforming the surface tissue of a cavity to a desired shape in order to permit the volume of tissue surrounding applicator head 30 to be treated with a predefined dose of radiation. The convex shape of applicator head 30 can also be selected to closely approximate the shape of the cavity to be treated, rather than to conform the cavity to head 30. The applicator system 10 can also include a low energy filter 34 (shown in FIG. 3) for absorbing low energy radiation.

Figure 1B:
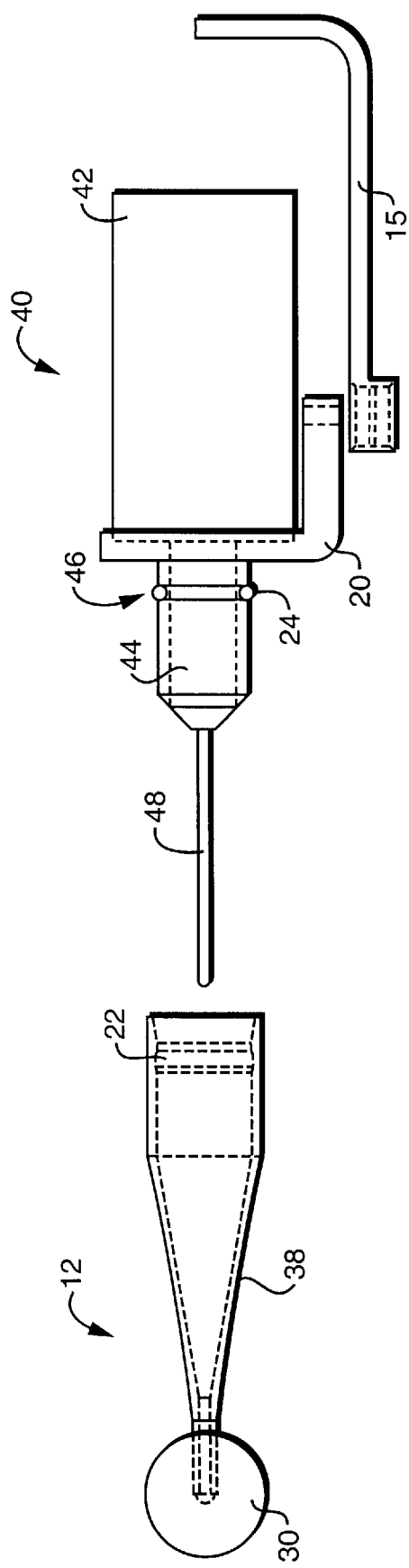
FIG. 1B is a diagrammatic exploded view of the applicator system of FIG. 1A and a prior art radiation source, with the applicator system adapter coupled to the radiation source.

FIG. 1B shows adapter 20 of applicator system 10 mounted on a radiation source, such as a miniature x-ray source 40. The x-ray source 40 includes a housing 42, a barrel 44 and an elongated probe 48. The x-ray source 40 is adapted for generating a field of radiation having a predefined dose profile about the distal end of probe 48. The applicator system 10 is adapted to fit over probe 48 and barrel 44 of the x-ray source 40.

In FIG. 1B, adapter 20 is shown supported by a carrier support system arm 15, the carrier support system thereby supporting the radiosurgery system. The adapter includes a circumferential groove 46 and a retaining spring 24 (or O-ring) mounted in groove 46. A portion of spring 24 extends above the surface of the adapter 44 to facilitate engagement of applicator 12 to adapter 20. The proximate end of the applicator shank 38 is adapted to fit over adapter 20 and includes an interior, circumferential groove 22 which is adapted to receive the portion of the spring 24 that extends above the adapter groove 46.

Figure 2A:
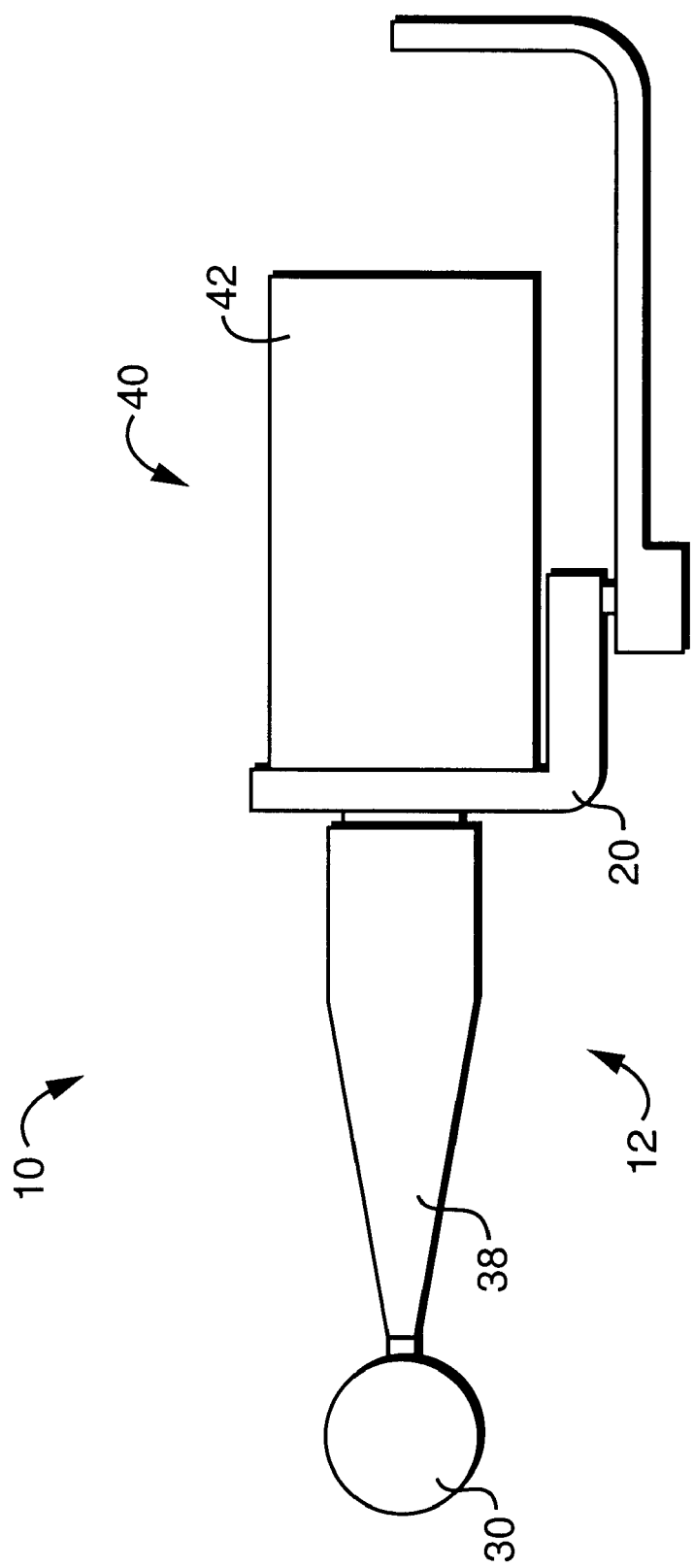
FIG. 2A is a diagrammatic view of the applicator system and radiation source of FIG. 1B in assembled form.
Figure 2B:
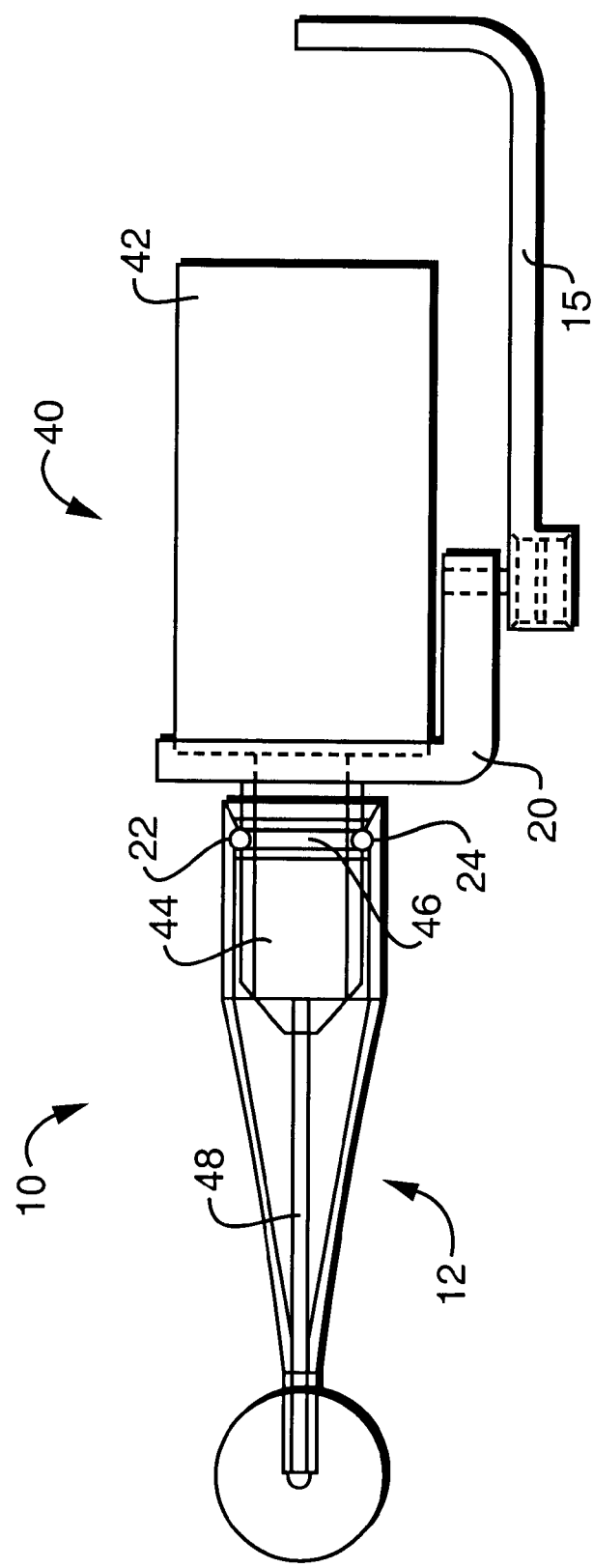
FIG. 2B is a diagrammatic cross-sectional view of the applicator system mounted to the radiation source of FIG. 2A.

As shown in FIGS. 2A and 2B, the applicator 12 slidably fits over and couples to adapter 20, which is secured to the x-ray source 40. When applicator 12 is slid onto adapter 20, spring 24 is compressed by the interior surface of shank 38 and, once groove 22 aligns with spring 24, the spring expands to fill groove 22, thereby securely coupling shank 38 of applicator 12 to adapter 20. Consequently, applicator 12 is secured over probe 48 of the x-ray source 40. As a person having ordinary skill will appreciate, other well known coupling methods and mechanisms can be used, for example: a,bayonet coupling, a threaded coupling, spring loaded ball bearings and detents, and set screws.

Figure 3:
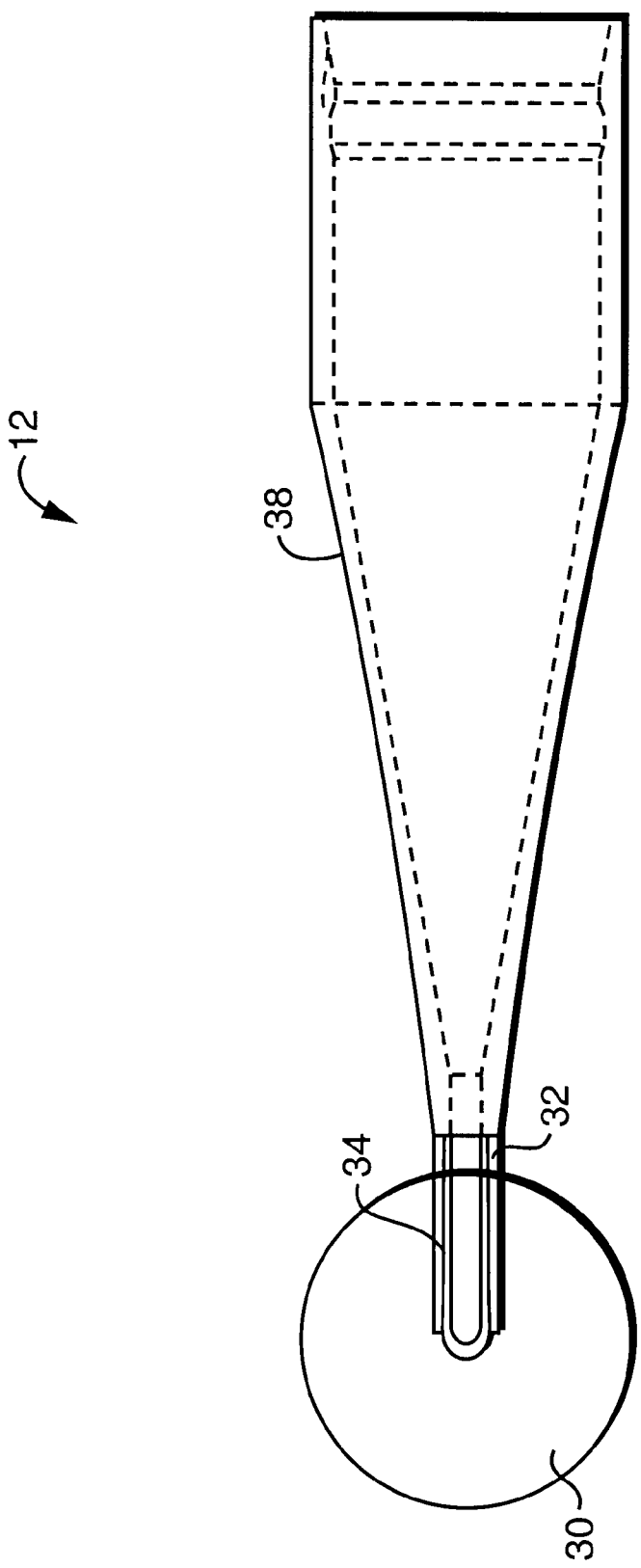
FIG. 3 is a diagrammatic cross sectional view of the applicator portion of the applicator system of FIG. 2B.

A proximate end of the applicator head 30 is adapted to receive probe 48. As shown in FIG. 3, the applicator shank 38 includes an applicator barrel 32 which supports applicator head 30. The applicator 12 may further include a low energy radiation filter 34 that is formed from a material that absorbs or blocks low energy radiation produced by the probe 48 in order to prevent adverse effects on tissue adjacent the applicator head 30. The shape of the low energy filter 34 is determined by the output profile of the radiation source in the radiation probe 48. Preferably, the shape of the low energy filter 34 is selected to reduce the low energy radiation produced outside the applicator head 30 to an acceptable level for the required treatment. For applicator systems with large applicator heads, a low energy filter may not be required because the applicator head may be sufficiently sized to attenuate the low energy radiation.

The applicator 12 can be formed (such as by molding or machining) from a single piece of material or from several pieces that are fastened together using, for example, a biocompatible epoxy. The applicator 12 is formed from a biocompatible material, such as Ultem-1000, a polyetherimide available from General Electric Plastics of Schenectady, N.Y. Preferably, the shank 38 and barrel 32 are either molded or machined from a single piece of material and the filter 34 and the applicator head 30 are separate components fixed in place using a biocompatible epoxy (such as Epo-Tek 353-ND available from Epo-Tek of Billerica, Mass.). The low energy filter is, in the preferred embodiment, formed from an aluminum material and the x-ray source 40 is that of a photon radiosurgery system (PRS) available from Photoelectron Corp. of Lexington, Mass.

FIG. 4 shows an example of a kit 50 containing a plurality of applicators 12A–12D, the kit may also include an adapter 20 (not shown). Each applicator can include a different size and/or shape applicator head, as may be used to treat multiple sites of different forms. In kit 50, applicator 12A includes a spherical shaped applicator head and applicators 12B–12D include ellipsoidal shaped applicator heads of differing size. Those skilled in the art will appreciate that applicators having a head of different shape and size to that shown in FIG. 4 may also be used, primarily as a function of any of a variety of considerations, such as the shape and size of the site or sites to be radiated and/or the predetermined desired radiation pattern and dose to be delivered.

Generally, it is desirable for the radiation dose delivered across the surface of the applicator head to be substantially uniform over substantially its entire surface. As an example, for spherical surface applicator heads, this is accomplished by selecting a radiation probe that produces a substantially spherical radiation dose profile. One method of producing ellipsoidal radiation dose profiles with ellipsoidal applicator heads and a probe which produces a spherical radiation dose profile is to vary the density of the applicator head material to filter the radiation and, thereby, modify the spherical dose profile in order to produce an ellipsoidal dose profile.

Figures 5A, 5B:
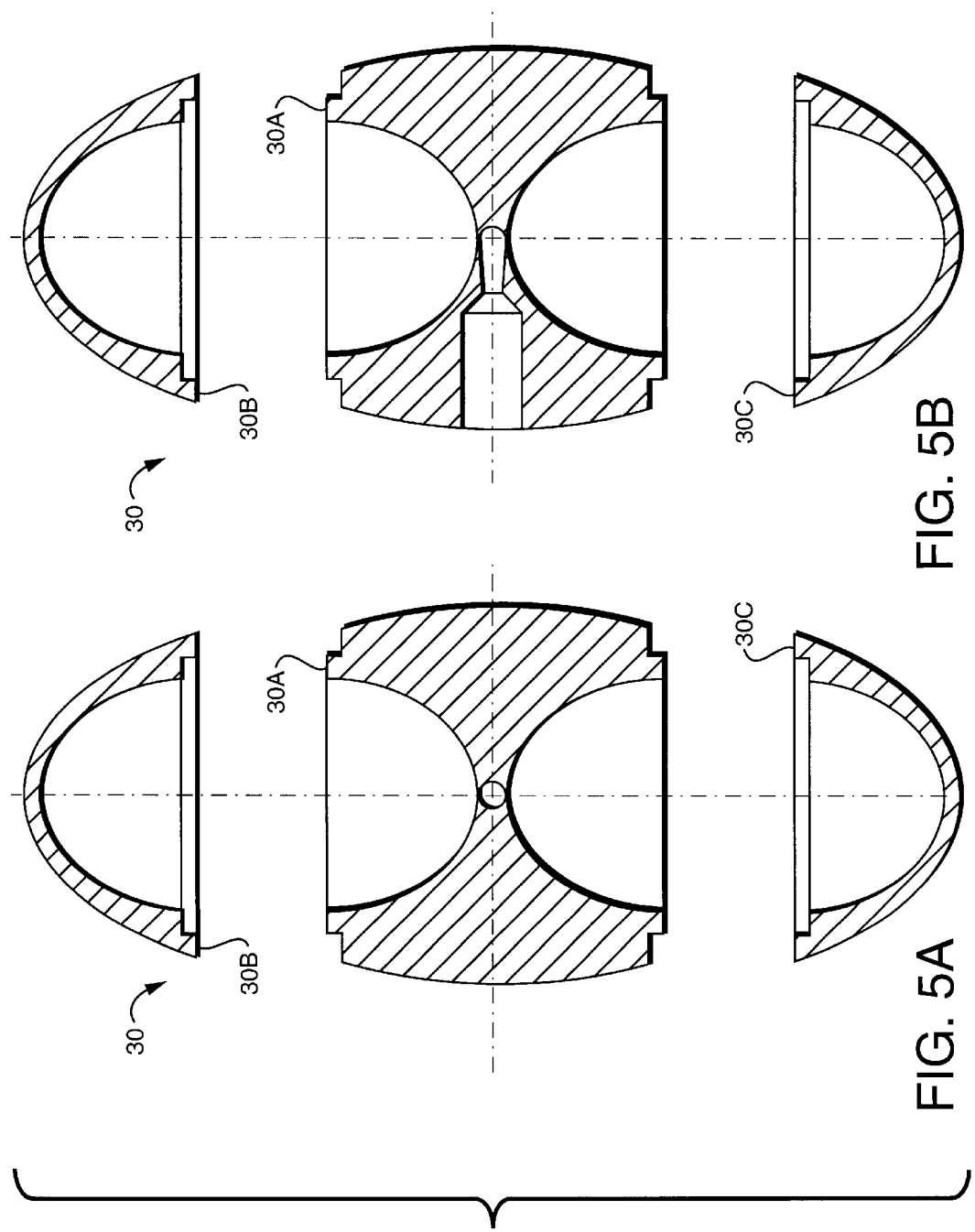
FIGS. 5A and 5B show diagrammatic views of an ellipsoidal applicator head, in accordance with present invention.

FIGS. 5A and 5B show an alternative construction of an applicator head 30 in accordance with the present invention, from a front view and a side view, respectively. The applicator head 30 can be constructed from three pieces that form an ellipsoidal outer surface and permit portions located within the applicator structure to be hollowed out. The applicator head 30 is formed by joining outer sections 30B and 30C to central section 30A, such as for example, using a biocompatible epoxy. The size and shape of hollowed out portions are determined by the total thickness of material along the path between the radiation source (not shown) and the surface of the applicator head 30 in order to provide the desired substantially uniform radiation dose profile. Preferably, the applicator head 30 is constructed from a biocompatible material such as Ultem-1000.

Figure 6:
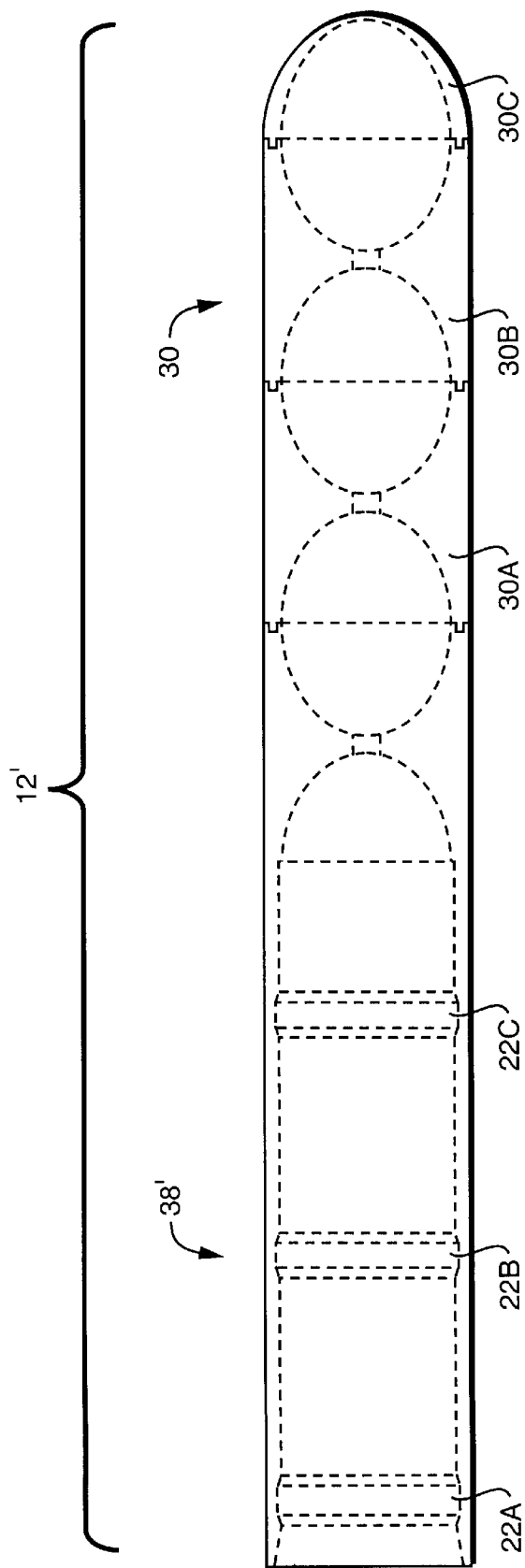
FIG. 6 shows a diagrammatic view of a cylindrical applicator system according to an alternate embodiment of the present invention.

FIG. 6 shows an alternate applicator system 12' which is adapted for producing a cylindrically shaped radiation dose profile with a cylindrical applicator head. The applicator system 12' includes an elongated shank 38' which includes multiple interior, circumferential grooves 22A, 22B, 22C and is adapted to be positioned at multiple, predefined positions relative to the radiation source, perhaps along a relatively fixed applicator adapter (not shown), wherein the adapter is secured to the barrel of the radiation source, as shown previously. In such an applicator system, the adapter must be of sufficient length to accommodate the length and multiple grooves of the applicator. The aggregate of the dosages of radiation applied at each successive position by the radiation probe can produce a cylindrical or similar radiation dose profile. Treatment is accomplished by positioning applicator 12' adjacent the area to be treated and positioning the adapter, coupled to the x-ray source, such that the retaining spring of the adapter expands within groove 22A, which defines a first coupling position, and then applying a predefined dose of radiation. The adapter and radiation probe is moved to successive positions 22B and 22C within the shank 38' and successive doses of radiation are applied to adjacent areas, producing a substantially cylindrical radiation dose profile, expanding radially from the probe.

Preferably, in a manner similar to the embodiment shown in FIGS. 5A and 5B, the applicator head 30 can be constructed from multiple sections 30A, 30B and 30C which permits portions to be hollowed out in order to provide a predefined radiation dose profile. Preferably, the applicator head 30 is constructed from a biocompatible material such as Ultem-1000 and the sections 30A, 30B, 30C can be fastened together and to shank 38, such as for example, using the biocompatible epoxy.

During treatment, the x-ray source 40 with the attached applicator system 10 may be supported by a gimbal mounted support system such as that disclosed in commonly owned U.S. patent application Ser. No. 09/502,473, which is hereby incorporated by reference. Such an arrangement allows a physician applying treatment to guide the tip of the applicator without having to support the weight of the device for the duration of the treatment. An example of such a system is the carrier support system shown in part in FIGS. 1B, 2A and 2B.

The above described system can be used to treat the site where a tumor or a portion of a tumor was removed with a predefined dose of radiation. The treatment involves inserting the applicator head into the site and delivering a continuous or intermittent dose of radiation to the tissue adjacent the exterior surface of the applicator head. Preferably, the shape of the applicator head is selected to closely match the shape of the excised tumor in order to support the surrounding tissue and provide accurate application of the radiation dose.

The invention may be embodied in other specific forms without departing from the spirit or essential characteristics thereof. For example, the adapter of the applicator system could be integral with the radiation source or the shank. Additionally, the applicator system may include only the applicator, without the adapter. The present embodiments are therefore to be considered in respects as illustrative and not restrictive, the scope of the invention being indicated by the appended claims rather than by the foregoing description, and all changes which come within the meaning and range of the equivalency of the claims are therefore intended to be embraced therein.

What is claimed is:

1. A radiation applicator system for use with a radiation source for facilitating the application of a dose of radiation to an area to be treated, said radiation applicator system comprising:
   A) an applicator, adapted to substantially encase a radiating probe tip of said radiation source, said applicator including:
      i) a shank having a proximate end and a distal end; and
      ii) a substantially rigid head secured to said shank distal end and having a void region therein for receiving said probe tip, and having a convex surface for engaging said area to be treated by said dose of radiation, wherein said head has a size, shape and density configured to provide absorption to define a predefined dose profile of radiation in response to radiation emitted from said probe tip when said probe tip is disposed in said void region.

2. A radiation applicator system according to claim 1 wherein said probe is an elongated probe and said radiation source includes a housing having said elongated probe extending from said housing.

3. A radiation applicator system according to claim 1 wherein said applicator head defines a substantially spherical treatment surface.

4. A radiation applicator system according to claim 1 wherein said head defines a substantially ellipsoidal treatment surface.

5. A radiation applicator system according to claim 1 wherein said head defines a substantially cylindrical treatment surface.

6. A radiation applicator system according to claim 1 wherein said head includes a plurality of interconnected elements.

7. A radiation applicator system according to claim 6 wherein said head includes a central element coupled to said adapter and a plurality of outer elements fixed to said central element.

8. A radiation applicator system according to claim 7 wherein said central element and at least one of said plurality of outer elements includes a hollowed portion.

9. A radiation applicator system according to claim 7 wherein said central element and said plurality of outer elements include adjacent hollowed portions.

10. A radiation applicator system according to claim 1 wherein said head is formed from a material having a predefined thickness at predefined locations.

11. A radiation applicator system according to claim 1 further comprising a low energy filter, coupled to said applicator head and adapted to attenuate low energy radiation emitted from said probe tip.

12. A radiation applicator system according to claim 1 wherein said shank includes a fastening element adapted to fasten said applicator at a first predefined position with respect to said radiation source.

13. A radiation applicator system according to claim 1 wherein said shank includes a fastening element adapted to fasten said applicator in a plurality of positions with respect to said radiation source.

14. A radiation applicator system according to claim 13 wherein said head is adapted to produce a radiation dose profile having a substantially cylindrical shape.

15. A radiation applicator system according to claim 13 wherein said head includes a plurality of interconnected elements.

16. A radiation applicator system according to claim 13 wherein said applicator head is formed from a material having a predefined thickness at predefined locations over the surface of said applicator head.

17. A radiation applicator system according to claim 1 further comprising:
  B) an adapter, including:
    i) a first coupler suited for mated engagement with said shank proximate end; and
    ii) a second coupler suited for mated engagement with said radiation source.

18. A kit for applying radiation to an area to be treated, said kit comprising:
  a radiation source adapted for producing a predefined radiation dose; and
  a plurality of radiation applicator systems, each of said radiation applicator systems including:
    A) an applicator, adapted for substantially encasing a radiating probe tip, said applicator including:
      i) a shank having a proximate end and a distal end; and
      ii) a substantially rigid head secured to said shank distal end and having a void region therein for receiving said probe tip, and having a convex surface for engaging said area to be treated by said dose of radiation, wherein said head has a size, shape and density configured to provide absorption to define a predefined dose profile of radiation in response to radiation emitted from said probe tip when said probe tip is disposed in said void region.

19. A kit according to claim 18 wherein the applicator head of at least one of the plurality of applicator systems is different in size or cross-sectional shape than the applicator head of at least one of the other applicator systems from the plurality of applicator systems.

20. A kit according to claim 18 wherein the applicator head of each of the plurality of applicator systems is different in size or cross-sectional shape than the applicator head of the each of the other applicator systems from the plurality of applicator systems.

21. A kit according to claim 18 further comprising:
  B) an adapter, including:
    i) a first coupler suited for mated engagement with said shank proximate end, and
    ii) a second coupler suited for mated engagement with said radiation source.

22. A radiation applicator system for use with a radiation source for facilitating the application of a dose of radiation to an area to be treated, said radiation applicator system comprising:
  A) an applicator, adapted to substantially encase a radiating probe tip of said radiation source, said applicator including:
    i) a shank having a proximate end and a distal end; and
    ii) a substantially rigid head secured to said shank distal end and having a void region therein for receiving said probe tip, and having a convex surface for engaging said area to be treated by said dose of radiation, wherein said head has a size, shape and density configured to provide absorption to define a predefined dose profile of radiation in response to radiation emitted from said probe tip when said probe tip is disposed in said void region; and
  B) an adapter, including:
    i) a first coupler suited for mated engagement with said shank proximate end, and
    ii) a second coupler suited for mated engagement with said radiation source.

* * * * *